US011357557B2

(12) United States Patent
Cross, III

(10) Patent No.: US 11,357,557 B2
(45) Date of Patent: Jun. 14, 2022

(54) BONE JOINT REAMING TOOL

(71) Applicant: Mayo Foundation for Medical Education and Research, Rochester, MN (US)

(72) Inventor: William W. Cross, III, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 541 days.

(21) Appl. No.: 16/029,894

(22) Filed: Jul. 9, 2018

(65) Prior Publication Data

US 2018/0317988 A1 Nov. 8, 2018

Related U.S. Application Data

(63) Continuation of application No. 14/790,480, filed on Jul. 2, 2015, now Pat. No. 10,045,803.

(60) Provisional application No. 62/020,528, filed on Jul. 3, 2014.

(51) Int. Cl.
| | |
|---|---|
| *A61B 17/16* | (2006.01) |
| *A61B 17/86* | (2006.01) |
| *A61B 17/88* | (2006.01) |
| *A61B 17/70* | (2006.01) |
| *A61B 90/00* | (2016.01) |
| *A61F 2/30* | (2006.01) |

(52) U.S. Cl.
CPC ........ *A61B 17/863* (2013.01); *A61B 17/1617* (2013.01); *A61B 17/1671* (2013.01); *A61B 17/7055* (2013.01); *A61B 17/8811* (2013.01); *A61B 90/06* (2016.02); *A61B 17/864* (2013.01); *A61F 2002/30995* (2013.01)

(58) Field of Classification Search
CPC . A61B 17/16; A61B 17/1615; A61B 17/1617; A61B 17/1662; A61B 17/1671
See application file for complete search history.

(56) References Cited

U.S. PATENT DOCUMENTS

| | | |
|---|---|---|
| 644,286 A | 2/1900 | Eyster |
| 2,136,471 A | 11/1938 | Schneider |
| 2,168,854 A | 8/1939 | Agnew |

(Continued)

FOREIGN PATENT DOCUMENTS

| | | |
|---|---|---|
| AU | 675525 B | 9/1994 |
| AU | 2007200961 A1 | 3/2007 |

(Continued)

OTHER PUBLICATIONS

AO Surgery Reference. "Lag screw principles". May 10, 2011. Web. Accessed Mar. 9, 2018.

(Continued)

*Primary Examiner* — Si Ming Ku

(57) ABSTRACT

A sacroiliac joint fusion screw and associated delivery tools and method. Embodiments of the sacroiliac joint fusion screw comprise a shaft having proximal and distal end portions and a head on the proximal end of the shaft. A threaded portion on a distal portion of the shaft is configured to engage a sacrum. A glide zone portion on the shaft between the threaded portion and the proximal end portion is configured to extend through an ilium. The screw can provide stability and compression to the joint.

15 Claims, 5 Drawing Sheets

(56) References Cited

U.S. PATENT DOCUMENTS

| | | |
|---|---|---|
| 3,025,853 A | 3/1962 | Mason |
| 4,103,683 A | 8/1978 | Neufeld |
| 4,569,338 A | 2/1986 | Edwards |
| 4,612,918 A | 9/1986 | Slocum |
| 4,770,376 A | 9/1988 | Lindblom |
| 4,787,378 A | 11/1988 | Sodhi |
| 4,898,186 A | 2/1990 | Ikada et al. |
| 4,978,349 A | 12/1990 | Frigg |
| 4,992,010 A | 2/1991 | Fischer |
| 5,000,165 A | 3/1991 | Watanabe |
| 5,015,255 A | 5/1991 | Kuslich |
| 5,030,220 A | 7/1991 | Howland |
| 5,034,011 A | 7/1991 | Howland |
| 5,192,282 A | 3/1993 | Draenert |
| 5,242,444 A | 9/1993 | MacMillan |
| 5,253,965 A | 10/1993 | Angel |
| 5,300,074 A | 4/1994 | Frigg |
| 5,304,190 A | 4/1994 | Reckelhoff et al. |
| 5,306,275 A | 4/1994 | Bryan |
| 5,334,205 A | 8/1994 | Cain |
| 5,350,391 A | 9/1994 | Iacovelli |
| 5,375,957 A | 12/1994 | Golledge |
| 5,445,639 A | 8/1995 | Kuslich et al. |
| 5,591,170 A | 1/1997 | Spievack et al. |
| 5,593,407 A | 1/1997 | Reis |
| 5,620,456 A | 4/1997 | Sauer et al. |
| 5,632,746 A | 5/1997 | Middleman et al. |
| 5,649,947 A | 7/1997 | Auerbach et al. |
| 5,725,581 A | 3/1998 | Brånemark |
| 5,741,256 A | 4/1998 | Bresina |
| 5,908,422 A | 6/1999 | Bresina |
| 5,928,239 A | 7/1999 | Mirza |
| 5,968,062 A | 10/1999 | Thomas et al. |
| 5,993,477 A | 11/1999 | Vaitekunas et al. |
| 6,030,406 A | 2/2000 | Davis et al. |
| 6,036,695 A | 3/2000 | Smith |
| 6,039,761 A | 3/2000 | Li et al. |
| 6,053,916 A | 4/2000 | Moore |
| 6,059,785 A | 5/2000 | Schavan et al. |
| 6,187,007 B1 | 2/2001 | Frigg et al. |
| 6,197,028 B1 | 3/2001 | Ray et al. |
| 6,319,253 B1 | 11/2001 | Ackeret et al. |
| 6,358,251 B1 | 3/2002 | Mirza |
| 6,379,360 B1 | 4/2002 | Ackeret et al. |
| 6,383,188 B2 | 5/2002 | Kuslich et al. |
| 6,409,730 B1 | 6/2002 | Green et al. |
| 6,428,539 B1 | 8/2002 | Baxter et al. |
| 6,440,138 B1 | 8/2002 | Reiley et al. |
| 6,565,566 B1 | 5/2003 | Wagner et al. |
| 6,635,059 B2 | 10/2003 | Randall et al. |
| 6,645,212 B2 | 11/2003 | Goldhahn et al. |
| 6,679,886 B2 | 1/2004 | Weikel et al. |
| 6,726,690 B2 | 4/2004 | Eckman |
| 6,740,090 B1 | 5/2004 | Cragg et al. |
| 6,746,451 B2 | 6/2004 | Middleton et al. |
| 6,814,734 B2 | 11/2004 | Chappuis et al. |
| 6,821,276 B2 | 11/2004 | Lambrecht et al. |
| 6,835,197 B2 | 12/2004 | Roth et al. |
| 6,863,694 B1 | 3/2005 | Boyce et al. |
| 6,899,716 B2 | 5/2005 | Cragg |
| 6,923,813 B2 | 8/2005 | Phillips et al. |
| 6,938,452 B2 | 9/2005 | Rudolph et al. |
| 6,939,351 B2 | 9/2005 | Eckman |
| 7,041,107 B2 | 5/2006 | Pohjonen et al. |
| 7,077,613 B2 | 7/2006 | Rudolph et al. |
| 7,179,024 B2 | 2/2007 | Greenhalgh |
| 7,182,765 B2 | 2/2007 | Roth et al. |
| 7,241,297 B2 | 7/2007 | Shaolian et al. |
| 7,264,622 B2 | 9/2007 | Michelson |
| 7,306,600 B2 | 12/2007 | Roth et al. |
| 7,410,488 B2 | 8/2008 | Janna et al. |
| 7,429,264 B2 | 9/2008 | Melkent et al. |
| 7,473,267 B2 | 1/2009 | Nguyen et al. |
| 7,476,226 B2 | 1/2009 | Weikel et al. |
| 7,478,987 B2 | 1/2009 | O'Banion et al. |
| 7,500,977 B2 | 3/2009 | Assell et al. |
| 7,575,588 B2 | 8/2009 | Barker et al. |
| 7,588,574 B2 | 9/2009 | Assell et al. |
| D601,711 S | 10/2009 | Lin |
| 7,608,077 B2 | 10/2009 | Cragg et al. |
| 7,641,658 B2 | 1/2010 | Shaolian et al. |
| 7,666,207 B2 | 2/2010 | Schläpfer et al. |
| 7,682,394 B2 | 3/2010 | Recoules-Arche et al. |
| 7,699,849 B2 | 4/2010 | Eckman |
| 7,749,225 B2 | 7/2010 | Chappuis et al. |
| 7,780,690 B2 | 8/2010 | Rehnke |
| 7,828,828 B2 | 11/2010 | Lim et al. |
| 7,833,246 B2 | 11/2010 | Mitchell |
| 7,867,233 B2 | 1/2011 | Shaolian et al. |
| 7,879,038 B2 | 2/2011 | Reiley et al. |
| 7,909,827 B2 | 3/2011 | Reiley et al. |
| 7,914,535 B2 | 3/2011 | Assell et al. |
| 7,914,545 B2 | 3/2011 | Ek |
| 7,922,765 B2 | 4/2011 | Reiley |
| 7,951,163 B2 | 5/2011 | Ek |
| RE42,757 E | 9/2011 | Kuslich et al. |
| 8,034,055 B2 | 10/2011 | Cragg |
| 8,052,613 B2 | 11/2011 | Assell et al. |
| 8,070,750 B2 | 12/2011 | Wenstrom et al. |
| 8,092,505 B2 | 1/2012 | Sommers |
| 8,109,957 B2 | 2/2012 | Stad et al. |
| 8,114,084 B2 | 2/2012 | Betts |
| 8,202,305 B2 | 6/2012 | Reiley |
| 8,221,424 B2 | 7/2012 | Cha |
| 8,262,710 B2 | 9/2012 | Freedman et al. |
| 8,298,264 B2 | 10/2012 | Betz et al. |
| 8,308,779 B2 | 11/2012 | Reiley |
| 8,323,293 B2 | 12/2012 | Morgan et al. |
| 8,348,950 B2 | 1/2013 | Assell et al. |
| 8,353,910 B2 | 1/2013 | Dell'Oca |
| 8,353,911 B2 | 1/2013 | Goldin et al. |
| 8,361,003 B2 | 1/2013 | Reiley |
| 8,388,667 B2 | 3/2013 | Reiley et al. |
| 8,409,205 B2 | 4/2013 | Yang et al. |
| 8,414,648 B2 | 4/2013 | Reiley |
| 8,425,570 B2 | 4/2013 | Reiley |
| 8,439,925 B2 | 5/2013 | Marino et al. |
| 8,444,693 B2 | 5/2013 | Reiley |
| 8,470,004 B2 | 6/2013 | Reiley |
| 8,480,675 B2 | 7/2013 | Betts |
| RE44,501 E | 9/2013 | Janna et al. |
| 8,523,865 B2 | 9/2013 | Reglos et al. |
| 8,523,892 B2 | 9/2013 | Rehnke et al. |
| 8,551,093 B2 | 10/2013 | Roth et al. |
| 8,551,171 B2 | 10/2013 | Johnson et al. |
| 8,556,902 B2 | 10/2013 | Ek et al. |
| 8,562,651 B2 | 10/2013 | Metcalf et al. |
| 8,568,414 B2 | 10/2013 | Siravo et al. |
| 8,591,549 B2 | 11/2013 | Lange |
| 8,696,672 B2 | 4/2014 | Barnhouse et al. |
| 8,734,456 B2 | 5/2014 | Stark |
| 8,734,462 B2 | 5/2014 | Reiley et al. |
| 8,734,487 B2 | 5/2014 | Bhatnagar et al. |
| 8,778,026 B2 | 7/2014 | Mauldin |
| 8,808,293 B2 | 8/2014 | Buettler et al. |
| 8,840,623 B2 | 9/2014 | Reiley |
| 8,840,631 B2 | 9/2014 | Messmer |
| 8,840,651 B2 | 9/2014 | Reiley |
| 8,845,638 B2 * | 9/2014 | Siegal ................ A61B 17/1631 606/80 |
| 8,852,241 B2 | 10/2014 | Datta |
| 8,858,601 B2 | 10/2014 | Reiley |
| 8,882,818 B1 | 11/2014 | Vestgaarden |
| 8,920,477 B2 | 12/2014 | Reiley |
| 8,926,615 B2 | 1/2015 | Ek |
| 9,101,366 B2 | 8/2015 | Sterrett et al. |
| 9,101,371 B2 | 8/2015 | Assell et al. |
| 9,113,919 B2 | 8/2015 | Assell et al. |
| 9,149,283 B2 | 10/2015 | Assell et al. |
| 9,161,763 B2 | 10/2015 | Assell et al. |
| 9,345,488 B2 | 5/2016 | Assell et al. |
| 9,375,323 B2 | 6/2016 | Reiley |
| 9,445,842 B2 | 9/2016 | Cianfrani et al. |
| 9,445,855 B2 | 9/2016 | Lin et al. |

(56) References Cited

U.S. PATENT DOCUMENTS

| | | |
|---|---|---|
| 9,662,124 B2 | 5/2017 | Assell et al. |
| 9,700,356 B2 | 7/2017 | Donner et al. |
| 9,713,478 B2 | 7/2017 | Assell et al. |
| 9,833,321 B2 | 12/2017 | Rindal et al. |
| 10,045,803 B2 | 8/2018 | Cross, III |
| 2001/0034526 A1 | 10/2001 | Kuslich et al. |
| 2001/0049527 A1 | 12/2001 | Cragg |
| 2002/0082605 A1 | 6/2002 | Reiley et al. |
| 2003/0181982 A1 | 9/2003 | Kuslich |
| 2003/0191474 A1 | 10/2003 | Cragg et al. |
| 2004/0064058 A1 | 4/2004 | McKay |
| 2004/0267269 A1 | 12/2004 | Middleton et al. |
| 2005/0137600 A1 | 6/2005 | Jacobs et al. |
| 2005/0159746 A1 | 7/2005 | Grob et al. |
| 2005/0177167 A1 | 8/2005 | Muckter |
| 2005/0182417 A1 | 8/2005 | Pagano |
| 2005/0267482 A1 | 12/2005 | Hyde |
| 2006/0054171 A1 | 3/2006 | Dall |
| 2006/0111780 A1 | 5/2006 | Petersen |
| 2006/0149247 A1 | 7/2006 | Frigg et al. |
| 2006/0155289 A1 | 7/2006 | Windhager et al. |
| 2006/0241629 A1 | 10/2006 | Krebs et al. |
| 2007/0123889 A1 | 5/2007 | Malandain et al. |
| 2007/0198020 A1 | 8/2007 | Reiley et al. |
| 2007/0255231 A1 | 11/2007 | Gross et al. |
| 2007/0260270 A1 | 11/2007 | Assell et al. |
| 2007/0270879 A1 | 11/2007 | Isaza et al. |
| 2007/0299445 A1 | 12/2007 | Shadduck et al. |
| 2008/0009823 A1 | 1/2008 | McKay |
| 2008/0009861 A1 | 1/2008 | Stark |
| 2008/0009875 A1 | 1/2008 | Sankaran et al. |
| 2008/0091199 A1 | 4/2008 | Cragg |
| 2008/0114364 A1 | 5/2008 | Goldin et al. |
| 2008/0243122 A1 | 10/2008 | Kohm et al. |
| 2008/0243126 A1 | 10/2008 | Gutierrez et al. |
| 2008/0269754 A1 | 10/2008 | Lutz et al. |
| 2008/0294167 A1 | 11/2008 | Schumacher et al. |
| 2009/0054898 A1 | 2/2009 | Gleason |
| 2009/0093883 A1 | 4/2009 | Carrasco |
| 2009/0138053 A1 | 5/2009 | Assell et al. |
| 2009/0198237 A1 | 8/2009 | Downey et al. |
| 2009/0216238 A1 | 8/2009 | Stark |
| 2009/0259261 A1 | 10/2009 | Reiley |
| 2009/0319043 A1 | 12/2009 | McDevitt et al. |
| 2010/0030216 A1 | 2/2010 | Arcenio |
| 2010/0131011 A1 | 5/2010 | Stark |
| 2010/0168748 A1 | 7/2010 | Knopp et al. |
| 2010/0241123 A1 | 9/2010 | Middleton et al. |
| 2011/0028978 A1 | 2/2011 | Li et al. |
| 2011/0082548 A1 | 4/2011 | Assell et al. |
| 2011/0087294 A1 | 4/2011 | Reiley |
| 2011/0087296 A1 | 4/2011 | Reiley et al. |
| 2011/0098709 A1 | 4/2011 | Malandain et al. |
| 2011/0106170 A1 | 5/2011 | Doerr |
| 2011/0118796 A1 | 5/2011 | Reiley et al. |
| 2011/0166575 A1 | 7/2011 | Assell et al. |
| 2011/0172772 A1 | 7/2011 | Abdou |
| 2011/0178552 A1 | 7/2011 | Biscup et al. |
| 2011/0264229 A1 | 10/2011 | Donner |
| 2011/0295272 A1 | 12/2011 | Assell et al. |
| 2011/0319899 A1 | 12/2011 | O'Neil et al. |
| 2012/0010624 A1 | 1/2012 | O'Halloran et al. |
| 2012/0022535 A1 | 1/2012 | Mayer et al. |
| 2012/0022568 A1 | 1/2012 | Koblish et al. |
| 2012/0029518 A1 | 2/2012 | Blackwell et al. |
| 2012/0095560 A1 | 4/2012 | Donner |
| 2012/0130429 A1 | 5/2012 | Mitchell |
| 2012/0191191 A1 | 7/2012 | Trieu |
| 2012/0259363 A1 | 10/2012 | Lange et al. |
| 2012/0259366 A1 | 10/2012 | Lange |
| 2012/0271357 A1 | 10/2012 | Arthur et al. |
| 2012/0323285 A1 | 12/2012 | Assell et al. |
| 2013/0018376 A1 | 1/2013 | Yoon et al. |
| 2013/0018427 A1 | 1/2013 | Pham et al. |
| 2013/0035723 A1 | 2/2013 | Donner |
| 2013/0053902 A1 | 2/2013 | Trudeau |
| 2013/0138214 A1 | 5/2013 | Greenhalgh et al. |
| 2013/0144343 A1 | 6/2013 | Arnett et al. |
| 2013/0165935 A1 | 6/2013 | Griffiths et al. |
| 2013/0172736 A1 | 7/2013 | Abdou |
| 2013/0197587 A1 | 8/2013 | Abdou |
| 2013/0218215 A1 | 8/2013 | Ginn et al. |
| 2013/0231746 A1 | 9/2013 | Ginn et al. |
| 2013/0237988 A1 | 9/2013 | Mauldin |
| 2013/0238093 A1 | 9/2013 | Mauldin et al. |
| 2013/0245703 A1 | 9/2013 | Warren et al. |
| 2013/0245763 A1 | 9/2013 | Mauldin |
| 2013/0267836 A1 | 10/2013 | Mauldin et al. |
| 2013/0267961 A1 | 10/2013 | Mauldin et al. |
| 2013/0267989 A1 | 10/2013 | Mauldin et al. |
| 2013/0296953 A1 | 11/2013 | Mauldin et al. |
| 2013/0338774 A1 | 12/2013 | Coale |
| 2014/0012330 A1 | 1/2014 | Johnson, II et al. |
| 2014/0012340 A1 | 1/2014 | Beck et al. |
| 2014/0031934 A1 | 1/2014 | Trieu |
| 2014/0031935 A1 | 1/2014 | Donner et al. |
| 2014/0046330 A1 | 2/2014 | Goldin et al. |
| 2014/0046380 A1 | 2/2014 | Asfora |
| 2014/0074167 A1 | 3/2014 | Trautwein et al. |
| 2014/0081280 A1 | 3/2014 | Lin et al. |
| 2014/0088707 A1 | 3/2014 | Donner et al. |
| 2014/0121707 A1 | 5/2014 | Stark |
| 2014/0135772 A1 | 5/2014 | Goldin et al. |
| 2014/0135850 A1 | 5/2014 | Parent et al. |
| 2014/0135927 A1 | 5/2014 | Pavlov et al. |
| 2014/0171949 A1 | 6/2014 | Attar |
| 2014/0200618 A1 | 7/2014 | Donner et al. |
| 2014/0207240 A1 | 7/2014 | Stoffman et al. |
| 2014/0222150 A1 | 8/2014 | Reiley |
| 2014/0236310 A1 | 8/2014 | Stark |
| 2014/0249589 A1 | 9/2014 | Reiley et al. |
| 2014/0257297 A1* | 9/2014 | Koogle, Jr. ........ A61B 17/1668 606/80 |
| 2014/0257298 A1 | 9/2014 | Reiley |
| 2014/0257415 A1 | 9/2014 | Reiley |
| 2014/0276844 A1 | 9/2014 | Bourque et al. |
| 2014/0276846 A1 | 9/2014 | Mauldin et al. |
| 2014/0276851 A1 | 9/2014 | Schneider et al. |
| 2014/0277165 A1 | 9/2014 | Kalzman et al. |
| 2014/0277204 A1 | 9/2014 | Sandhu |
| 2014/0277460 A1 | 9/2014 | Schifano et al. |
| 2014/0277463 A1 | 9/2014 | Yerby et al. |
| 2014/0288605 A1 | 9/2014 | Mesiwala et al. |
| 2014/0303628 A1 | 10/2014 | Middleton et al. |
| 2014/0324052 A1 | 10/2014 | Carrison et al. |
| 2014/0330382 A1 | 11/2014 | Mauldin |
| 2014/0336763 A1 | 11/2014 | Donner et al. |
| 2014/0358188 A1 | 12/2014 | Larson et al. |
| 2014/0379037 A1 | 12/2014 | Datta |
| 2015/0005832 A1 | 1/2015 | Reiley |
| 2015/0005881 A1 | 1/2015 | Connor et al. |
| 2015/0012000 A1 | 1/2015 | Siegal et al. |
| 2015/0157367 A1 | 6/2015 | Biedermann |
| 2015/0157377 A1 | 6/2015 | Pham et al. |
| 2015/0164514 A1 | 6/2015 | Wlodarski et al. |
| 2015/0190149 A1 | 7/2015 | Assell et al. |
| 2015/0223847 A1 | 8/2015 | Trieu |
| 2015/0257770 A1 | 9/2015 | Assell et al. |
| 2015/0282817 A1 | 10/2015 | Osman et al. |
| 2015/0289913 A1 | 10/2015 | Vaidya |
| 2015/0327872 A1 | 11/2015 | Assell et al. |
| 2016/0000488 A1 | 1/2016 | Cross et al. |
| 2016/0038201 A1 | 2/2016 | Cummings |
| 2016/0081810 A1 | 3/2016 | Reiley et al. |
| 2016/0120661 A1 | 5/2016 | Schell et al. |
| 2017/0007306 A1 | 1/2017 | Werner |
| 2017/0007409 A1 | 1/2017 | Mauldin et al. |
| 2017/0303938 A1 | 10/2017 | Rindal et al. |
| 2017/0303972 A1 | 10/2017 | Schumacher et al. |
| 2017/0304060 A1 | 10/2017 | Rindal et al. |
| 2017/0348108 A1 | 12/2017 | Schumacher et al. |
| 2018/0055645 A1 | 3/2018 | Rindal et al. |
| 2018/0153698 A1 | 6/2018 | Rindal et al. |

(56) References Cited

U.S. PATENT DOCUMENTS

FOREIGN PATENT DOCUMENTS

| | | |
|---|---|---|
| AU | 2014201339 B2 | 10/2014 |
| CA | 2414168 C | 1/2002 |
| DE | 202009006906 U1 | 8/2009 |
| EP | 0369603 B1 | 5/1990 |
| EP | 0641548 B1 | 3/1995 |
| EP | 0719114 A1 | 7/1996 |
| EP | 1123056 B1 | 8/2001 |
| EP | 2560566 B1 | 2/2013 |
| EP | 2575642 A1 | 4/2013 |
| EP | 2693990 A1 | 2/2014 |
| EP | 2774556 A1 | 9/2014 |
| IN | 201302786 P1 | 11/2014 |
| WO | 9619945 A1 | 7/1996 |
| WO | 0158629 A1 | 8/2001 |
| WO | 0234147 A1 | 5/2002 |
| WO | 02091909 A2 | 11/2002 |
| WO | 2005063951 A1 | 7/2005 |
| WO | 2007016684 A2 | 2/2007 |
| WO | 2007142830 A2 | 12/2007 |
| WO | 2008021319 A2 | 2/2008 |
| WO | 2008021656 A2 | 2/2008 |
| WO | 2008054752 A2 | 5/2008 |
| WO | 2008103839 A2 | 8/2008 |
| WO | 2009029074 A1 | 3/2009 |
| WO | 2009143496 A1 | 11/2009 |
| WO | 2010017631 A1 | 2/2010 |
| WO | 2010065015 A1 | 6/2010 |
| WO | 2011014135 A2 | 2/2011 |
| WO | 2012036872 A2 | 3/2012 |
| WO | 2012174541 A1 | 12/2012 |
| WO | 2013131493 A1 | 9/2013 |
| WO | 2013134652 A2 | 9/2013 |
| WO | 2013134775 A1 | 9/2013 |
| WO | 2013134778 A1 | 9/2013 |
| WO | 2013166496 A1 | 11/2013 |
| WO | 2014137679 A1 | 9/2014 |
| WO | 2014140782 A2 | 9/2014 |
| WO | 2014145725 A2 | 9/2014 |
| WO | 2017189377 A1 | 11/2017 |

OTHER PUBLICATIONS

Google Search Results for "orthopedic lag screw before Jul. 2, 2014". Web. Accessed Mar. 9, 2018.

Orthoped. "Lag Screw Fixation". Sep. 16, 2010. Web. Accessed Mar. 9, 2018.

Zhanle, Zheng; et al. "The Application of a Computer-Assisted Thermoplastic Membrane Navigation System in Screw Fixation of the Sacroiliac Joint—A Clinical Study." Injury, Int. J. Care Injured 43:495-499, 2012.

* cited by examiner

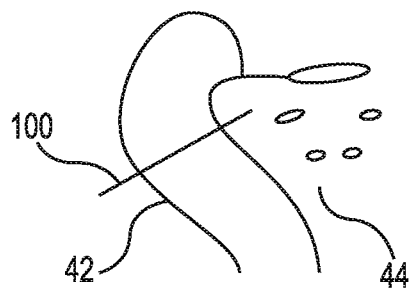
Fig. 6A
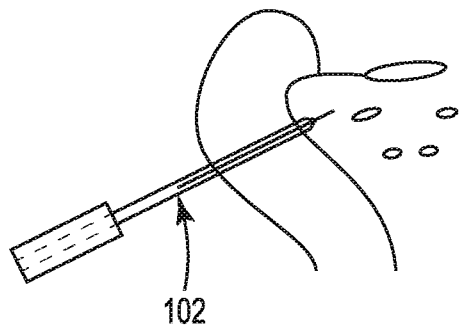
Fig. 6B
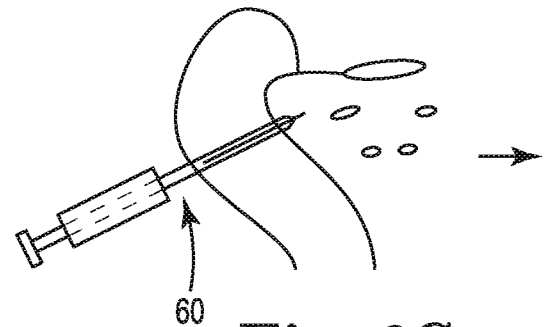 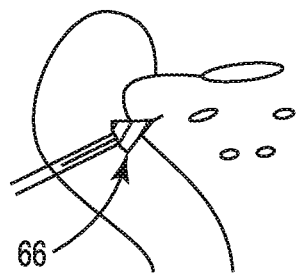
Fig. 6C  Fig. 6D
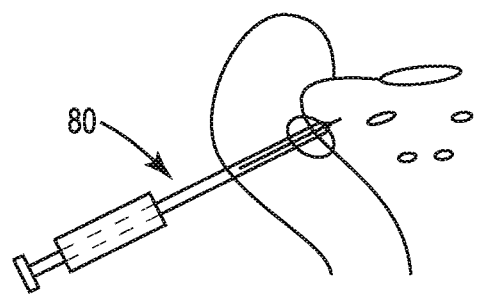
Fig. 6E

BONE JOINT REAMING TOOL

CROSS REFERENCE TO RELATED APPLICATION

This application is a continuation of U.S. application Ser. No. 14/790,480, filed Jul. 2, 2015 and entitled Sacroiliac Joint Fusion Screw And Method, which claims the benefit of U.S. Provisional Application Ser. No. 62/020,528 filed on Jul. 3, 2014 and entitled Sacroiliac Joint Fusion Screw And Method, which are incorporated herein by reference in their entireties and for all purposes.

TECHNICAL FIELD

The invention relates to surgical fasteners, instruments and methods. In particular, embodiments of the invention include screws, tools and methods for use in connection with sacroiliac joint fusion.

BACKGROUND

The sacroiliac joint is formed by the meeting of the sacrum (at the base of the spine) and the ilium (at the upper part of the pelvis). Treatment for indications such a pain at the sacroiliac joint includes fusing the sacrum and ilium together. The Assell et al. U.S. Patent Application Publication No. 2011/0166575, for example, discloses a sacroiliac fusion system including associated surgical instruments and methods. A bone screw that can be used in connection with sacroiliac fusion procedures is disclosed in the Assell et al. U.S. Patent Application Publication No. 2012/0323285. Both of the above-identified Assell patent application publications are incorporated herein by reference for all purposes. There remains a continuing need for improved sacroiliac joint fusion fasteners (such as screws) and associated instruments and procedures.

SUMMARY

Embodiments of the invention include improved sacroiliac joint fusion screws and associated delivery tools and methods. Embodiments of the sacroiliac joint fusion screw comprise a shaft having proximal and distal end portions and a head on the proximal end of the shaft. A threaded portion on a distal portion of the shaft is configured to engage a sacrum. A glide zone portion on the shaft between the threaded portion and the proximal end portion is configured to extend through an ilium. The screw can provide stability and compression to the joint.

BRIEF DESCRIPTION OF THE DRAWINGS

FIGS. 6A-6H are diagrammatic illustrations of steps in accordance with embodiments of the invention for using the instruments shown in FIGS. 3A, 3B, 4A, 4B and 5 to insert the joint fusion screw shown in FIG. 1.

DESCRIPTION OF THE INVENTION

Figure 1:
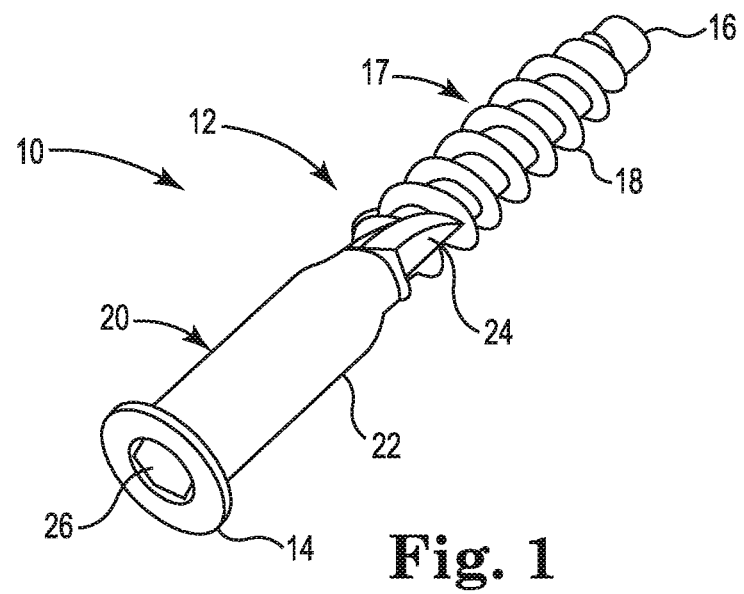
FIG. 1 is an isometric illustration of a joint fusion screw in accordance with embodiments of the invention.

FIG. 1 illustrates a fastener or screw 10 in accordance with embodiments of the invention. As shown, screw 10 includes a shank or shaft 12 having a first or proximal end with a head 14 and a second or distal end with a tip 16. A threaded portion 17 of the shaft 12 adjacent to the tip 16 (i.e., on a distal portion of the shaft) includes threads 18. A glide zone portion 20 of the shaft 12 adjacent to the head 14 (i.e., on a proximal portion of the shaft) is free from threads and in the illustrated embodiment has a generally smooth surface 22. The illustrated embodiment of the screw 10 also includes cutting threads 24 at the proximal end of the threaded portion 17 (e.g., adjacent to the glide zone portion 20) to facilitate removal of the screw 10. Other embodiments of the invention do not have the cutting threads 24. Similarly, embodiments of screw 10 (not shown) have self-tapping threads at the distal end of threaded portion 17 (i.e., near the tip 16). Head 14 includes a hex socket 26 that is configured to receive a hex key driver tool (not shown) that can be used to implant the screw 10. Other embodiments of the invention (not shown) include a head 14 having other driver tool-receiving structures such as a hex head or a hex cap.

Screw 10 can be fabricated from metal such as titanium or other suitable materials. The screw 10 can have any length suitable for the sacroiliac joint fusion applications. Embodiments of the screw 10 can, for example, have lengths from 45 mm to 95 mm at 5 mm increments. The diameter of the shaft 12 (i.e., a minor diameter) can be about 10 mm and the diameter of the threaded portion 17 (i.e., a major diameter at the threads 18) can be about 16 mm in embodiments. Other embodiments have larger and smaller major and minor diameters. Thread pitch ranges from about 2.25 mm to 2.5 mm, and thread depth ranges from about 2.8 mm to about 3 mm in embodiments, although the screws 10 can have larger and smaller thread pitch and depth. Screws 10 can also be cannulated. Some embodiments of screws 10 can, for example, have a cannula of about 2.5 mm in diameter, although other embodiments have larger and smaller openings. Head 14 will typically have a diameter that is larger than the diameter of the shaft 12. For example, some embodiments of screw 10 have a head 14 that is about 18 mm in diameter, although other embodiments have heads with larger or smaller diameter heads.

As described below, a function of the threaded portion 17 of the screw 10 is to engage the sacrum when implanted into the sacroiliac joint from the side of the ilium. Accordingly, the length of the threaded portion 17 can vary. A function of the glide zone portion 20 is to enable the screw 10 to provide compression to the sacroiliac joint. This function can be achieved by providing the screw 10 with glide zone lengths corresponding to the thickness of the ilium when the screw is implanted in the sacroiliac joint (i.e., the portion of the screw 10 that extends through and is adjacent to the ilium is free from threads). In one embodiment, the length of the glide zone portion is about 23 mm. The length of the glide zone portion 20 can be longer or shorter in other embodiments. The length of the glide zone portion 20 can be determined by measuring widths of ilia of patients (e.g., from CT scans) at the locations of the sacroiliac joint to be fused, and averaging those widths.

Figure 2:
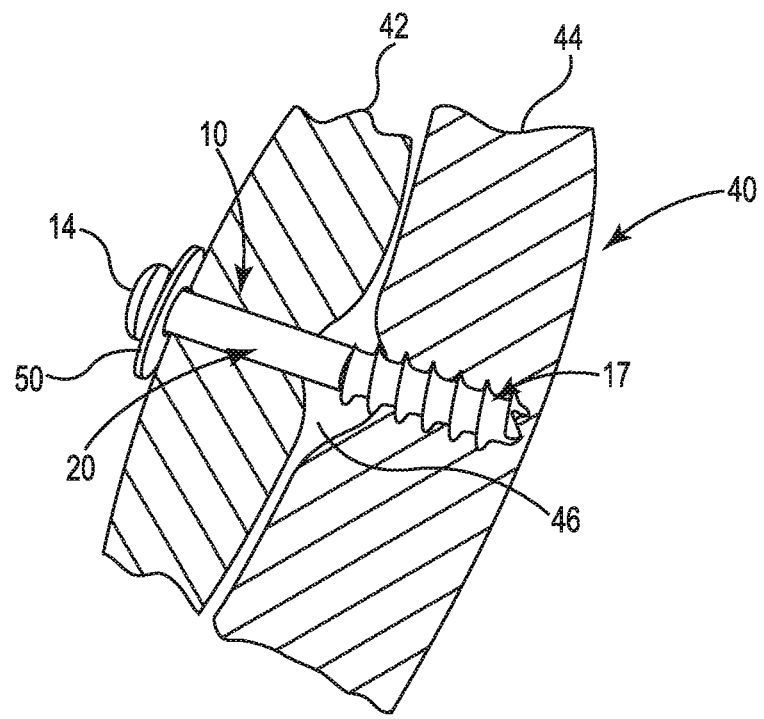
FIG. 2 is an illustration of a sacroiliac joint fused by the screw shown in FIG. 1 by methods in accordance with embodiments of the invention.

FIG. 2 illustrates a sacroiliac joint 40 fused by a screw 10 in accordance with embodiments of the invention. As shown, the sacroiliac joint 40 includes portions of an ilium 42 and a sacrum 44. The joint 40 is typically approached from the side with the ilium 42. Using a tool such as a drill (not shown), a pilot hole is bored through the ilium 42 and into the sacrum 44 at the location to be fused. A decortication procedure can optionally be performed to remove tissue from the ilium 42 and/or sacrum 44 in an area 46 (i.e., a decortication region) of the joint 40 to be fused (e.g., using a reamer or other tool such as that shown in application publication 2011/0166575 referred to above that is inserted into the pilot hole). Bone graft material can optionally be inserted into the area 46 (not shown).

Screw 10 can then be implanted into the joint 40 by using a driver to insert the screw into the pilot hole. As shown in FIG. 2, the threaded portion 17 of the screw 10 engages the sacrum 44, and the glide zone portion 20 extends through the ilium 42. Because the threaded portion 17 of the screw 10 is in purchase with the sacrum 44 and the head 14 is engaged with the ilium 42 while the portions of the ilium that the screw passes through are free from threads 18, the screw provides compression of the joint (i.e., the ilium and sacrum are urged together by the screw). In the illustrated embodiment a washer 50 is located on the shaft 12 between the screw head 14 and the ilium to increase the surface area of the engagement by the screw head. The compression provided by the screw 10 when implanted in accordance with the method described above allows significant compression across the sacroiliac joint 40. This enhanced compression can provide immediate patient comfort. Stability and joint preparation are also provided by this fusion method and device. For example, when using a screw such as 10 having a shaft 12 with a major diameter of 16 mm and a minor diameter of 10 mm, and a head 14 having an 18 mm diameter, an effective fusion radius of about 30 mm (14130 mm$^3$) can be achieved.

The amount of compression provided by the screw 10 can be maximized if the entire portion of the ilium 42 through which the screw 10 extends is free from purchase by threads 18. However, in some embodiments of the invention (not shown), substantial or efficacious amounts of compression can be achieved even if portions of the ilium 42 are purchased by threaded portion 17 of the screw. Should it be desired to remove screw 10, the cutting threads 24 will facilitate the removal by forming a leading path for the threads 18 between the cutting threads 24 and tip 16.

Additional apparatus and methods in connection with the invention are disclosed in the Appendix of the provisional application No. 62/020,528 identified above and incorporated herein by reference.

Figure 3B:
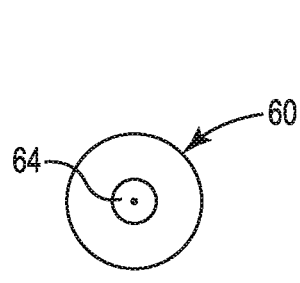
FIGS. 3A and 3B are side and end views, respectively, of a reaming instrument in accordance with embodiments of the invention, in a delivery or insertion state.
Figure 4B:
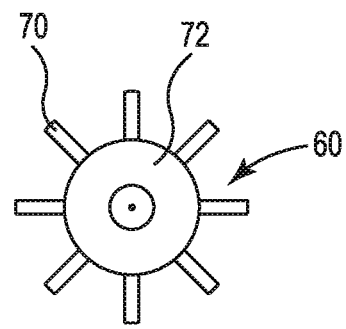
FIGS. 4A and 4B are side and end views, respectively, of the reaming instrument shown in FIGS. 3A and 3B, in an operational state.
Figure 3A:
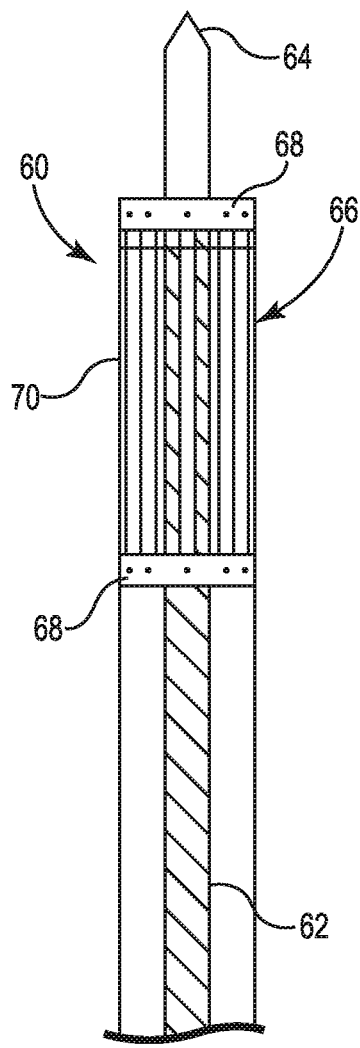
Figure 4A:
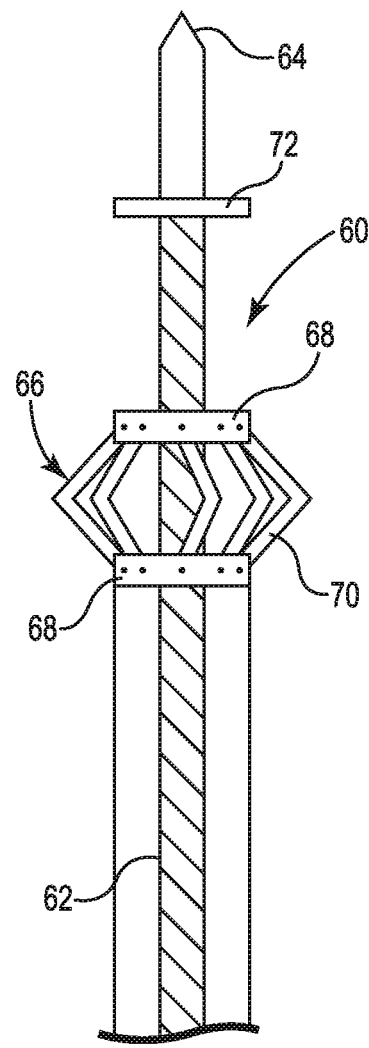

FIGS. 3A and 3B illustrate side and end views, respectively, of a reaming tool 60 in accordance with embodiments of the invention in a delivery state. FIG. 3A is a partial cross sectional view. FIGS. 4A and 4B illustrate side and end views, respectively, of the tool 60 in an operational state. As shown, the tool 60 has a central shaft 62 with a distal end 64, and a cutter 66 mounted to the shaft. The illustrated embodiment of cutter 66 has a mounts 68 coupled to the shaft 62, and a plurality of cutting blades 70 extending between the mounts. As shown, the opposite ends of the blades 70 are mounted to the mounts 68. Blades 70 are nitinol in embodiments, but can be other materials in other embodiments. In the delivery state shown in FIGS. 3A and 3B, the cutter 66 has a first, reduced diameter (e.g., about 10 cm in embodiments, generally equal to the minor diameter of the screw 10), with blades 70 in a generally linear configuration parallel one another and to the central shaft 62. As described below, when the reaming tool 60 is inserted into a surgical site at a sacroiliac joint and the cutter 66 is actuated, one or both of the mounts 68 move toward the other on the shaft 62, causing the blades 70 to deploy and flex outwardly to a non-linear configuration extending beyond the mounts 68, and the cutter 66 to take on a second, expanded diameter configuration (e.g., about 26 mm in embodiments) in the operational state shown in FIGS. 4A and 4B. In the illustrated embodiment the blades 70 have a generally triangular profile when the cutter 66 is deployed to the operational state, and the mount 68 that is adjacent to the distal end 64 slides toward the other mount (which can be fixed) to position the cutter at a predetermined location with respect to the distal end 64 of the tool 60. The location of the cutter 66 in the surgical site can thereby be more accurately determined. The embodiment shown in FIG. 4A has a shoulder member 72 that extends from the shaft 62 at a predetermined distance such as 1 cm from the distal end 64. The shoulder member 72 can aid in the positioning of the cutter 66. Other embodiments (not shown) include an actuator for moving the cutter 66 between the delivery and operational states.

Figure 5:
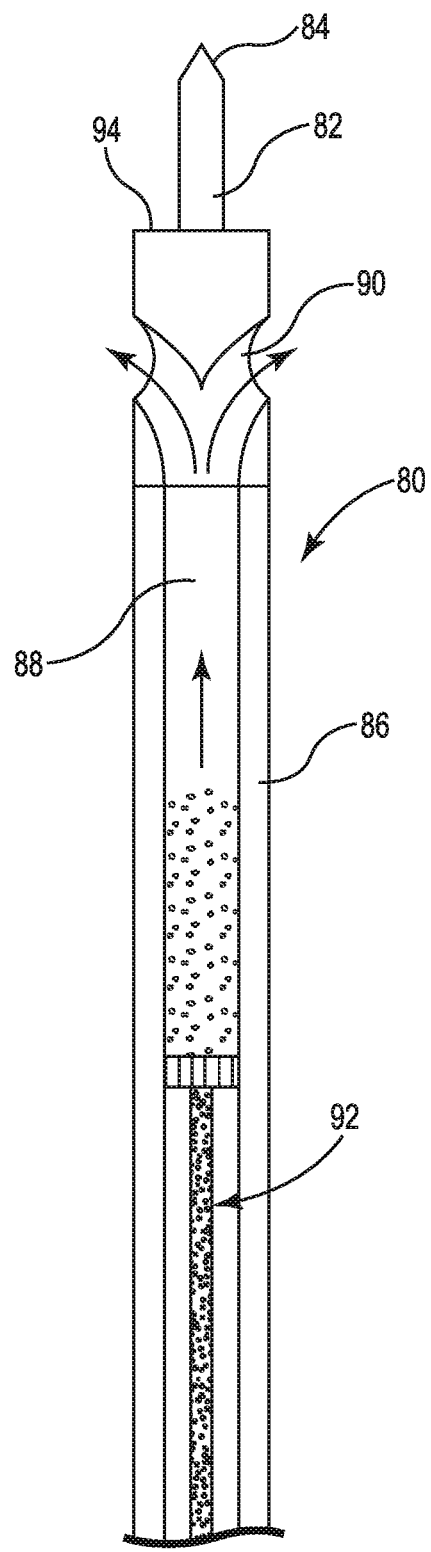
FIG. 5 is a side view of bone graft application tool in accordance with embodiments of the invention.

FIG. 5 is a partial cross sectional illustration of a bone graft application tool 80 in accordance with embodiments of the invention. The illustrated embodiment of the tool 80 has a shaft 82 with a distal end 84, a body 86 with a chamber 88 and one or more delivery openings 90 (two are shown in FIG. 5), and a plunger 92 in the chamber 88. The diameter of the body 86 can be about equal to the minor diameter of the screw 10 (e.g., about 10 mm). The body 86 has a shoulder 94 positioned at a location with respect to the distal end 84 that will locate the delivery openings 90 at locations corresponding to voids created by the reaming tool 60 in sacroiliac joints (e.g., the openings 90 of can be located at about the same distance from the distal end 84 of tool 80 as the expanded diameter portion of the cutter 66 is located from the distal end 64 of the reaming tool 60). As shown in FIG. 5, the delivery openings 90 extend from the exterior of the body 86, and communicate with the chamber 88. As described below, during sacroiliac joint fusion procedures, bone graft material (e.g., autograft material from initial drilling into bone of the patient) can be inserted into the chamber 88, and the plunger 92 actuated to deliver the bone graft material to the fusion site through the openings 90.

Figure 6F:
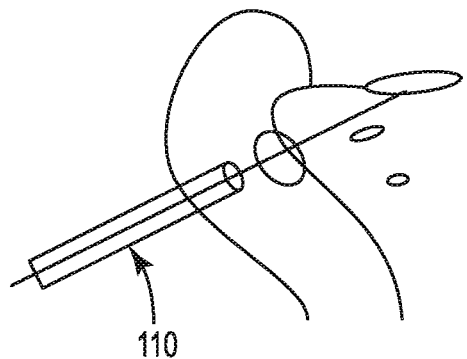

A sacroiliac joint fusion method in accordance with embodiments of the invention can be described with reference to FIGS. 6A-6H. As shown in FIG. 6A, a pin 100 can be inserted through the ilium 42 and into the sacrum 44 to define a path to the joint at the desired fusion surgical site. Using the pin 100 as a guide path, a drill 102 (e.g., 10.25 mm in diameter in embodiments) can be used to bore a pilot hole through the ilium 42 and sacrum 44 at the fusion site (FIG. 6B). The ilium 42 and/or sacrum 44 can be decorticated at the fusion site. FIGS. 6C and 6D, for example, illustrate the use of reaming tool 60 for decortication. As shown in FIG. 6C, the reaming tool 60 is inserted into the pilot hole with the cutter 66 in the delivery state. When the tool 60 is manipulated to locate cutter 66 at the desired position, the tool 60 is actuated to deploy the cutter to its operational state, and the tool is actuated (e.g., rotated) to remove portions of the ilium 42 and/or sacrum 44. Following the decortication procedure the reaming tool 60 is actuated to return the cutter 66 to the delivery state, and the reaming tool is withdrawn from the patient. Bone graft material, for example autograft bone material collected from the patient during the boring step 6B and/or the decortication step 6D, can be inserted at the fusion site. FIG. 6E, for example, illustrates the use of bone graft application tool 80 to deliver bone graft material to the decorticated area of the fusion site. During the step illustrated generally by FIG. 6E, the bone graft application tool 80 can be manipulated to position the delivery openings 90 at the location of any decorticated portions of the ilium 42 and sacrum 44.

Figure 6G:
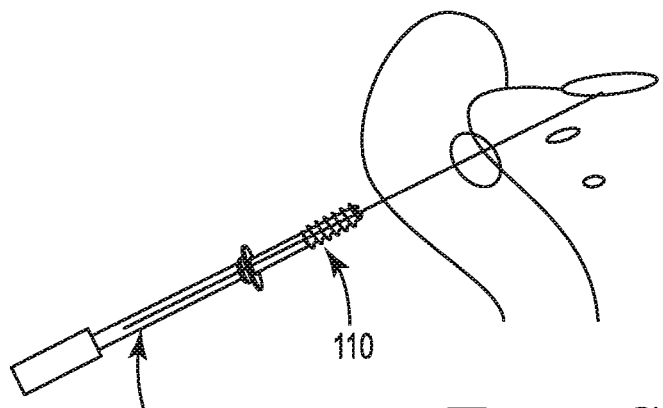
Figure 6H:
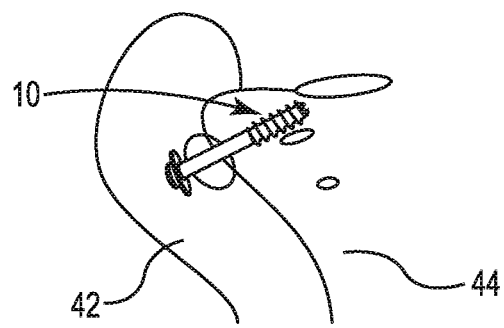

As shown in FIG. 6F, an instrument such as 110 can be used to measure the surgical site for purposes of determining an appropriate length for the screw 10. A screw 10 suitable for the fusion site is then selected, and inserted using a driver as shown in FIG. 6G. FIG. 6H, like FIG. 2, diagrammatically illustrates the screw 10 fusing the ilium 42 and sacrum 44 in accordance with embodiments of the invention. In embodiments, other methods are performed to insert screws 10. For example, in embodiments, the decortication and/or bone graft material delivery steps are not performed, and other procedures can be performed.

Although the invention has been described with reference to preferred embodiments, those skilled in the art will recognize that changes can be made in form and detail without departing from the spirit and scope of the invention.

The invention claimed is:

1. A joint reaming tool, comprising:
   a shaft comprising a proximal portion, an elongate distal tip portion, and a distal end on the elongate distal tip portion, wherein the tool is configured to be inserted into a joint leading with the distal end;
   a shoulder on a proximal end of the elongate distal tip portion of the shaft, proximal of the distal end;
   a cutter on the shaft, proximal of the shoulder, the cutter movable between a reduced diameter delivery state and an enlarged diameter operational state, wherein the cutter is configured to create voids in a joint when in the operational state, and including:
      a plurality of cutting blades including proximal and distal end portions; and
      wherein the cutting blades are generally linear and parallel to one another when the cutter is in the delivery state, and the cutting blades expand outwardly to a non-linear cutting configuration proximal of the shoulder by the distal end portions of the cutting blades moving away from the shoulder and toward the proximal end portions of the blades when the cutter is in the operational state.

2. The joint reaming tool of claim 1 wherein the cutting blades have a generally triangular cutting configuration profile when the cutter is in the operational state.

3. The joint reaming tool of claim 2, and further comprising an actuator for moving the cutter between the delivery state and the operational state.

4. The joint reaming tool of claim 1, further comprising a first mount moveable on the shaft, wherein the distal end portions of the cutting blades are mounted to the first mount, and the first mount moves toward the proximal end portion of the tool when the cutter is moved from the delivery state to the operational state.

5. The joint reaming tool of claim 4 wherein the cutting blades have a generally triangular cutting configuration profile when the cutter is in the operational state.

6. The joint reaming tool of claim 4, wherein the shoulder is configured to position the cutter.

7. The joint reaming tool of claim 4, further comprising a second mount, and wherein the proximal end portions of the cutting blades are mounted to the second mount.

8. The joint reaming tool of claim 7 wherein the second mount is fixedly positioned with respect to the shaft.

9. The joint reaming tool of claim 8, wherein the shoulder is configured to position the cutter.

10. The joint reaming tool of claim 9 wherein the cutting blades have a generally triangular cutting configuration profile when the cutter is in the operational state.

11. The joint reaming tool of claim 1, further comprising locating structure to locate the position the cutter with respect to the shoulder when the cutter is in the operational state.

12. The joint reaming tool of claim 1, further comprising for use with the joint reaming tool, a bone graft application tool comprising:
   a body;
   a chamber in the body to receive bone graft material;
   one or more delivery openings on the body in communication with the chamber;
   a shoulder on the body to locate the delivery openings at locations corresponding to the voids that can be created by the joint reaming tool in a joint.

13. The joint reaming tool and bone graft application tool of claim 12, the bone graft application tool further comprising a plunger actuatable to deliver bone graft material from the chamber through the one or more delivery openings.

14. The joint reaming tool and bone graft application tool of claim 12, wherein:
   the bone graft application tool further comprises a shaft extending from the body; and
   the shoulder of the bone graft application tool extends from the shaft.

15. The joint reaming tool and bone graft application tool of claim 14, the bone graft application tool further comprising a plunger actuatable to deliver bone graft material from the chamber through the one or more delivery openings.

* * * * *